(12) United States Patent
Feazel et al.

(10) Patent No.: US 7,229,034 B2
(45) Date of Patent: Jun. 12, 2007

(54) SEED CRUSHER

(75) Inventors: Rhonda J. Feazel, Brighton, IL (US);
John D. Hemphill, Ankeny, IA (US);
Sharon E. Malmberg, Crawfordsville, IA (US); Craig Mierkowski, Bridgeton, MO (US); Tavis Aholt, Washington, MO (US); Donald Sutter, Columbia, IL (US); Noel Harris, Arnold, MO (US)

(73) Assignee: Monsanto Technology LLC, St. Louis, MO (US)

( * ) Notice: Subject to any disclaimer, the term of this patent is extended or adjusted under 35 U.S.C. 154(b) by 177 days.

(21) Appl. No.: 11/071,091

(22) Filed: Mar. 3, 2005

(65) Prior Publication Data
US 2006/0196369 A1  Sep. 7, 2006

Related U.S. Application Data

(60) Provisional application No. 60/549,435, filed on Mar. 2, 2004.

(51) Int. Cl.
  *B02C 19/00* (2006.01)
(52) U.S. Cl. ................... 241/12; 241/21; 241/199.5; 241/199.11; 241/270

(58) Field of Classification Search .............. 241/6–12, 241/21, 169.2, 270, 199.1, 199.5, 199.8, 241/199.9, 199.11, 2, DIG. 27; 100/229 A
See application file for complete search history.

(56) References Cited

U.S. PATENT DOCUMENTS

| | | | | |
|---|---|---|---|---|
| 3,556,414 A | * | 1/1971 | Eberly, Jr. ..................... | 241/1 |
| 4,979,685 A | * | 12/1990 | Shioda et al. ................. | 241/65 |
| 5,533,683 A | * | 7/1996 | Fay et al. ..................... | 241/169 |
| 5,829,696 A | * | 11/1998 | DeStefano et al. ......... | 241/169 |
| 6,357,679 B1 | * | 3/2002 | Radke .......................... | 241/30 |

* cited by examiner

*Primary Examiner*—Mark Rosenbaum
(74) *Attorney, Agent, or Firm*—H. Shukla; Thomas E. Kelley

(57) ABSTRACT

A seed crusher e.g. useful in methods for high throughput analysis of seeds, comprises a horizontal well plate with at least one well for receiving a tube; an open-topped tube for lining each well wherein each tube is oriented for receiving a vertical reciprocating pin; a horizontal die plate with a vertical pin located to reciprocate in each tube; a removable separator for use in each tube to separate a reciprocating pin from a seed at the bottom of said tube and a press for bringing together the die plate and well plate to allow a pin to enter each tube.

8 Claims, 2 Drawing Sheets

SEED CRUSHER

This application claims the benefit of application No. U.S. 60/549,435 filed Mar. 2, 2004.

FIELD OF THE INVENTION

The present invention describes a seed crusher and its use in extraction of seed components.

BACKGROUND OF THE INVENTION

One of the goals of plant genetic engineering or conventional plant breeding is to produce plants with agronomically, horticulturally or economically important characteristics or traits. The testing of plant tissue for producing plants with improved desired characteristics often requires extraction of metabolites and other bio-molecules from soft tissue such as leaf or hard tissue such as seed. The first step in extraction from seed involves crushing which requires significant mechanical force for hard seeds. The manual application of force required for seed crushing in a high throughput screening is tedious, cumbersome, and usually a source of repetitive stress injuries.

SUMMARY OF THE INVENTION

This invention provides a seed crusher adapted for crushing seeds in tubes which can serve as containers for further analytical processing. More particularly, a seed crusher comprises; (a) a horizontal well plate with at least one well for receiving a tube; (b) an open-topped tube for lining each well, where each tube is oriented for receiving a vertical reciprocating pin; (c) a horizontal die plate with a vertical pin located to reciprocate in each tube; (d) a removable separator for use in each tube to separate a reciprocating pin from a seed at the bottom of said tube; and (e) a press for bringing together the die plate and well plate to allow a pin to enter each tube. In one embodiment the well plate is moveable and the die plate is fixed. In another embodiment the well plate is fixed and the die plate is moveable. In another embodiment the well plate has a plurality of wells and the seed crusher comprises a plurality of wells. Preferably the wells and tubes are in an array, which allows the plurality of tubes to be in a fixed structure. When the seed crusher comprises a plurality of wells and tubes, the die plate has a plurality of reciprocating pins, i.e. a pin aligned for reciprocating in each tube. Each well serves to hold and support the bottom of a tube, e.g. to prevent breakage from pushing a crushed seed through the bottom of a tube. In one embodiment the most of the tube can be located in a deep well. In another embodiment only the bottom of the tube lines the well.

The invention also provides a method of crushing seed by placing one or more seeds along with one or more removable separators in each tube and operating the seed crusher to reciprocate the pin in the tube. The invention further proves a method of extracting one or more constituents from crushed seed by the addition of an extraction medium in a tube with crushed seed and recovering the extraction medium from the tube.

DETAILED DESCRIPTION

Figure 1:
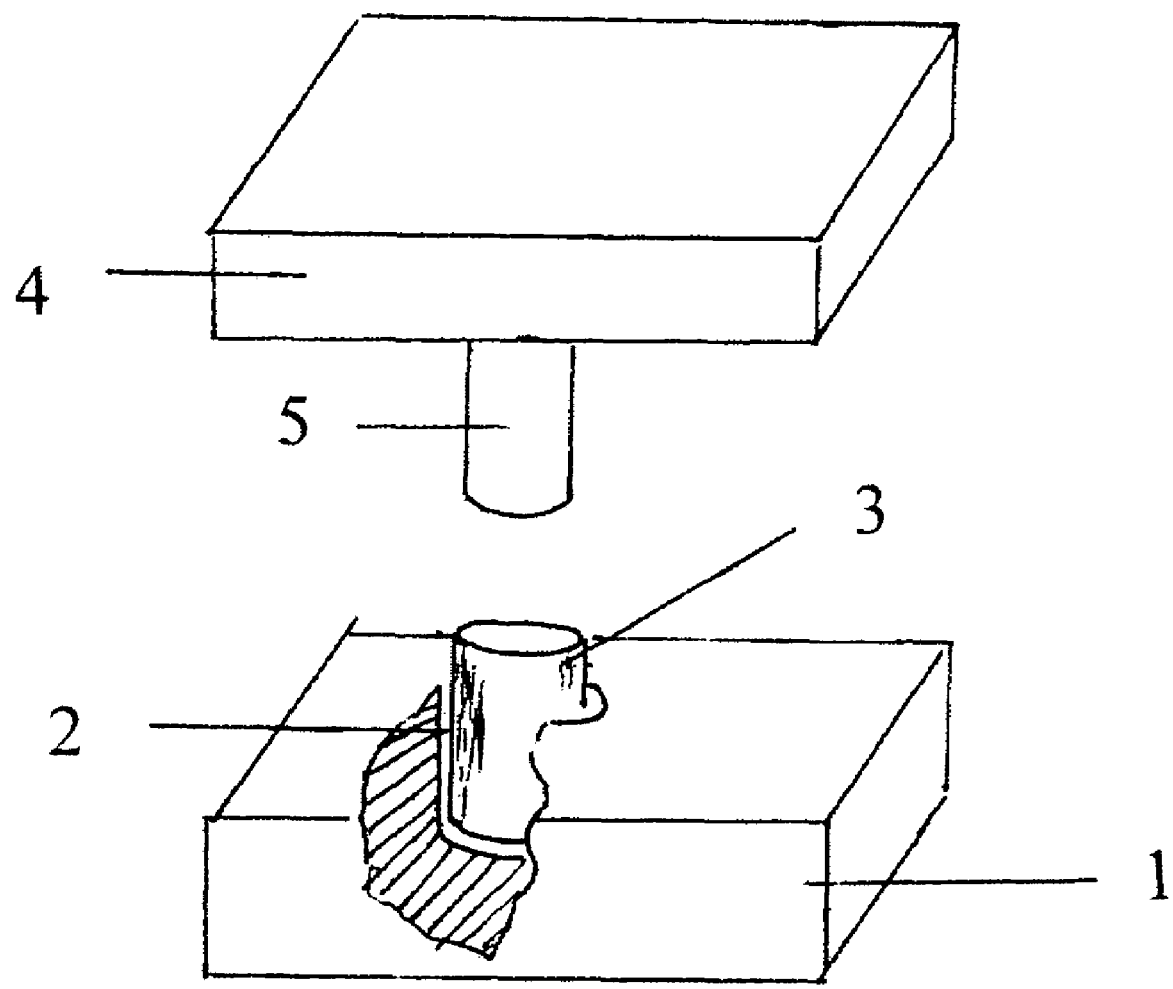
FIG. 1 is an illustration of components of a seed crusher.
Figure 2:
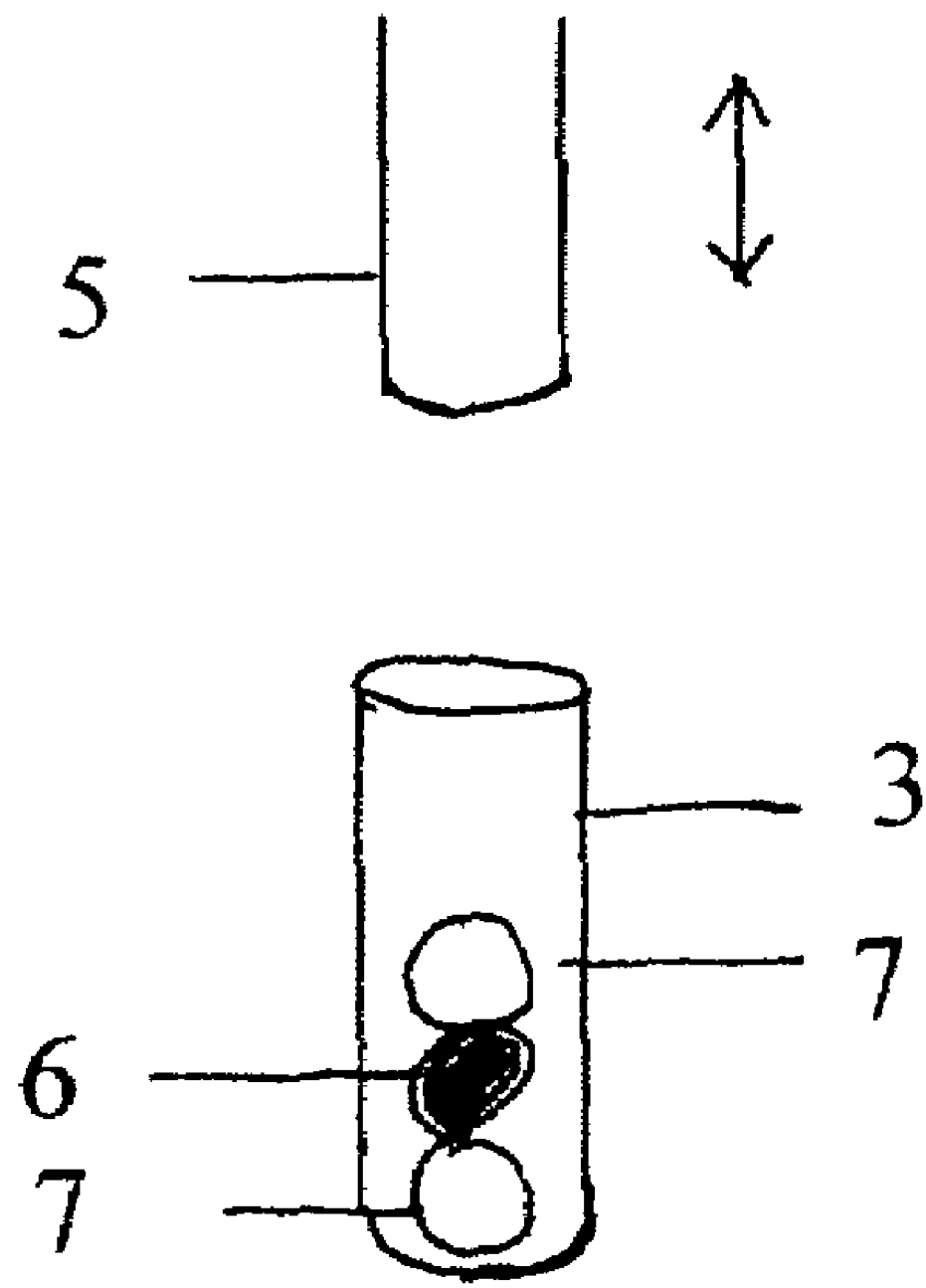
FIG. 2 is an illustration of a method of using a seed crusher.

With reference to FIGS. 1 and 2 there is shown a horizontal plate 1 having a well 2 supporting a tube 3. After a seed 6 and removable separator 7 is placed in a tube 3, a pin 5 attached to a die plate 4 reciprocates in the tube 3 sufficiently to crush the seed 6.

The function of the horizontal plate is to provide a strong base for tube-supporting wells. The horizontal plant can be static or moveable. The horizontal plate can be made of any material, which can withstand the pressure needed to crush seed in the tube, e.g. about 20-40 megaPascals [3,000 to 6,000 pounds per square inch]. A well plate can effectively be made from metal, e.g. steel or aluminum, or plastic, e.g. reinforced plastic. Each well in a well plate is designed to provide a relatively snug fit to conform to the base of a tube in order to prevent the brakeage of the tube. As tubes are preferably removable the well should be designed to facilitate easy removal of a tube.

An open-topped tube for use in the seed crusher has one open end for inserting and removing materials, e.g. seeds, separators and reciprocating pins, and one closed end to contain the contents of the tube. The shape of the bottom of the tube is such that it matches the shape of the well on the plate to provide a support to bottom of the tube by the well in the horizontal plate. The material of the tube is chosen to sustain the force applied by the reciprocating pin in order to maintain the integrity of the tube. Plastic such as polypropylene is a useful material of construction for tubes. In one embodiment a single tube fits a single well in the horizontal plate. In other embodiment an array of a plurality of tubes is in a unit, e.g. as a "multi-well" plate or a box with multiple tubes to fit corresponding multiple wells in the horizontal plate.

The die plate with a pin for each tube is designed to transfer the pressure from the die plate to pins contacting separators contacting seeds in the bottom of a tube. Each pin of the die plate is designed to reciprocate in a tube. The end of the pin that comes in contact with the separator is designed to transfer desired pressure to one or more seeds via one or more separators in the tube.

To effect seed crushing the horizontal plate and die plate are aligned so that, when the plates are pressed together, a pin will enter each tube as shown in FIG. 2, allowing a pin to press a separator onto a seed at the bottom of a tube. The plates can be mounted in a press where a compressing force is applied by hydraulic pistons, air pistons, electric driven screws, mechanical lever or mechanical driven screws. For rapid seed crushing a press with fast acting piston is preferred.

The amount of the force needed to crush one or more seeds is variable and depends on the variety of seed, size of the seed, shape of the seed, moisture content of the seed and the interaction between the pin and the seed via the separator. For the present invention a desired press will have properties where the amount of force can be varied to that required for adequately crushing the type of seed being processed. In one embodiment, the press is configured to apply a desired force to one or more seeds via a pin and one or more separators where the die plate is moveable and the horizontal plate is fixed. In other embodiment, the press is configured to apply a desired force to one or more seeds via a pin and one or more separators where the die plate is fixed and the horizontal plate is moveable.

The present invention also describes a method using the seed crusher for extraction of seed content. Extraction of components from seeds is done to perform further analysis of seed composition. Modern methods of analysis are very sensitive and are negatively impacted by cross contaminations. One or more separators are placed in the tube to avoid the contamination of the reciprocating pin and also for proper distribution of pressure on one or more seeds placed in the tube. The separator can be of any shape as long as it meets above criteria. A useful shape of a separator is spherical. One or more separators can be are placed between one or more seeds and the pin.

After crushing the seed by operation of the seed crusher, the pins are reciprocated out of the tubes and an extraction medium is delivered into each tube with crushed seed followed by the recovery of the extraction medium. Depending on the analysis the extraction medium can be a solvent, which is capable of dissolving the seed component under analysis; for example, an organic solvent will be a desired solvent if seed oil is the component under analysis. If seed component is a water-soluble salt, then the extraction medium can be water-based. The extraction medium can be delivered in the tube by any means capable of handling liquid such as a pipette, a dropper or a liquid handling robot. For increasing the efficiency of seed extraction, the extraction medium can be agitated along with the crushed seed content in the tube before the recovery of extraction medium from the tube.

We claim:

1. A seed crusher, comprising
   (a) a horizontal well plate with at least one well for receiving a tube;
   (b) an open-topped tube for lining each well wherein each tube is oriented for receiving a vertical reciprocating pin;
   (c) a horizontal die plate with a vertical pin located to reciprocate in each tube;
   (d) a removable separator for use in each tube to separate a reciprocating pin from a seed at the bottom of said tube; and
   (e) a press for bringing together the die plate and well plate to allow a pin to enter each tube.

2. The seed crusher of claim 1 wherein said well plate is moveable and said die plate is fixed.

3. The seed crusher of claim 1 wherein said well plate is fixed and said die plate is moveable.

4. The seed crusher of claim 1 wherein said well plate has a plurality of wells.

5. The seed crusher of claim 4 comprising a plurality of tubes fixed in an array.

6. A method of seed extraction using the seed crusher of claim 5 comprising the steps of:
   (a) placing at least one seed and a removable separator in each tube; wherein said separator transfers the pressure from said pin to the seed at the bottom of the tube;
   (b) operating the seed crusher to reciprocate the pin in said tube to crush the seed in the tube;
   (c) delivering extraction medium in each tube wherein said medium can dissolve seed components; and
   (d) recovering the extraction medium from each tube.

7. The method of claim 6 wherein said tube is shaken after delivering the extraction medium in the tube and before recovering the extraction medium from the tube.

8. The method of claim 7 wherein said extraction medium is delivered in a separate tube after recovering the extraction medium from the tube.

* * * * *